United States Patent [19]

Howarth et al.

[11] Patent Number: 4,715,715
[45] Date of Patent: Dec. 29, 1987

[54] SYSTEM FOR MEASURING THE COLOR OF A MATERIAL

[75] Inventors: John Howarth, Monte Sereno; Mark Alguard, Palo Alto, both of Calif.

[73] Assignee: Measurex Corporation, Cupertino, Calif.

[21] Appl. No.: 29,350

[22] Filed: Mar. 20, 1987

Related U.S. Application Data

[63] Continuation of Ser. No. 668,761, Nov. 6, 1984, abandoned.

[51] Int. Cl.⁴ .......................... G01N 21/86; G01J 3/46
[52] U.S. Cl. .................................... 356/402; 356/429; 356/243
[58] Field of Search ................ 356/402, 429, 243

[56] References Cited

U.S. PATENT DOCUMENTS

| | | | |
|---|---|---|---|
| 3,205,355 | 9/1965 | Ehlert | 356/243 X |
| 3,936,189 | 2/1976 | DeRemigis | 356/429 X |
| 4,033,698 | 7/1977 | Demsky et al. | 356/402 |
| 4,095,105 | 6/1978 | Rosenthal | 356/243 X |
| 4,243,319 | 1/1981 | Lodzinski | 356/429 X |
| 4,319,847 | 3/1982 | Howarth | 356/243 X |

Primary Examiner—Vincent P. McGraw
Attorney, Agent, or Firm—Hal J. Bohner

[57] ABSTRACT

A system is provided for measuring the color of a sample material, and the system includes means for illuminating the sample and a sensor to measure light from the sample. The system also includes sample backing means to receive light transmitted by the sample and reflect the light back to the sample.

7 Claims, 3 Drawing Figures

SYSTEM FOR MEASURING THE COLOR OF A MATERIAL

BACKGROUND OF THE INVENTION

1. The Field of The Invention

The present embodiment concerns a system and process for measuring the color of a material such as a sheet of paper.

2. State of the Art

During the production of many materials, the color of the material must be measured and controlled. For example, during the production of liquids such as paint or during the production of sheet materials such as plastics or paper, certain pigments are added to a base material to provide color, and the amount of each pigment must be carefully controlled to insure that the color is within specified standards.

U. S. Pat. No. 3,936,189 to De Remigis teaches a system for continuously monitoring the color of a moving sheet of paper. According to the patent an optical head includes a light integrating sphere for directing light from a source onto the web, and a plurality of sensing units are mounted in the upper portion of the sphere. On the opposite side of the sheet from the sensing unit is mounted an optical shoe providing black and white backgrounds. The black and white backgrounds are arranged to permit one or the other to be used to back the sheet during measurement of the color. The white background is produced by applying a white stripe to a quartz shoe.

We have found that systems such as those described in the patent using a white background in the form of paint or similar material can be inadequate for backing certain papers. That is, the measured color of a sheet of paper backed with a white standard such as white paint can vary significantly from the actual color of the sheet of paper.

OBJECTS OF THE INVENTION

An object of the present invention is to provide a means for measuring the color of a material backed by a standard to provide a highly accurate measurement of the color.

Further objects and advantages of the invention can be ascertained by reference to the specification and drawings herein which are offered by way of example and not in limitation of the invention which is defined by the claims and equivalents. BRIEF DESCRIPTION OF THE DRAWINGS FIG. 1 is a schematic illustration of the present embodiment.

DETAILED DESCRIPTION OF THE PREFERRED EMBODIMENT

Figure 1:
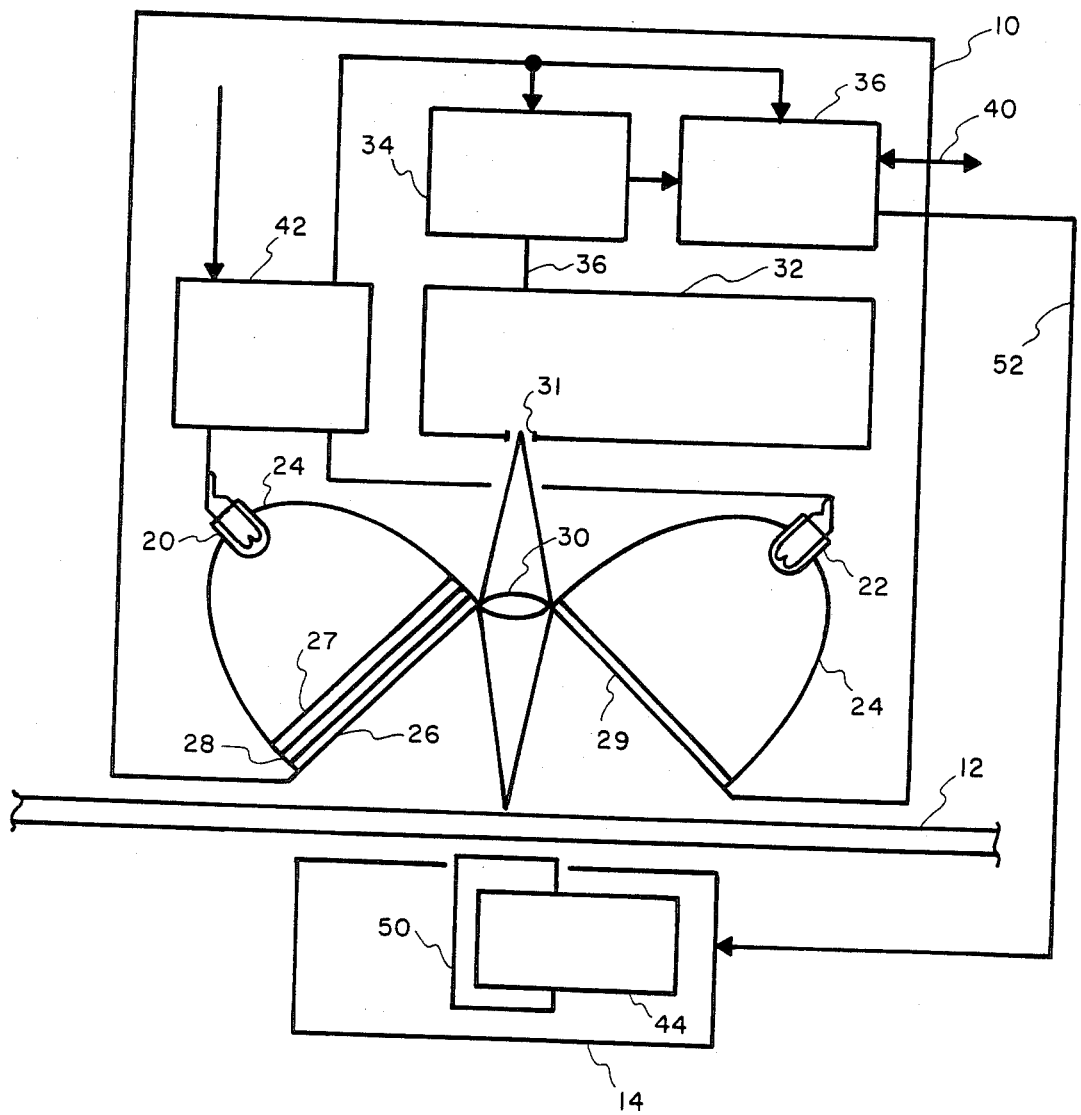

The embodiment shown in FIG. 1 includes a housing 10 which in practice can be mounted above a moving sheet of paper 12 for scanning back and forth across the sheet during the production of the paper. A second housing 14 is mounted to the side of the sheet of paper opposite the housing 10 and is constructed and arranged to move with the housing 10 so that the two housings 10 and 14 remain in alignment. This type of scanning system is conventional and is taught, for example, in U.S. Pat. No. 3,757,122.

Means for illuminating the sheet 12 is provided within the housing 10. The illumination means includes two light bulbs 20 and 22. The first light bulb 20 is a tungsten halide type to produce light in the visible range. The second light bulb 22 produces ultraviolet light. The light bulbs 20 and 22 are mounted in reflectors 24 which direct the light from the bulbs toward the sheet of paper 12. A plurality of filters are mounted in the reflectors 24. The filter 26 corrects the light from the bulb 20 to approximate C.I.E. illuminant "C", and the filter 27 absorbs some heat from the bulb 20 to prevent overheating of the filter 26. An air gap 28 is formed between filters 26 and 27. The filter 29 is a band-pass filter so that the light passing therethrough when added to the approximate C.I.E. illuminant "C" together produce light approximating C.I.E. illuminant $D_{65}$.

A lens 30 is mounted between the reflectors 24 for receiving light from the sheet of paper 12. The lens 30 is constructed so that light leaving a well-defined area on the paper is focused on the entrance slit 31 of spectral analyzer 32. The spectral analyzer 32 is conventional and includes a diffraction grating to break the light from lens 32 into its component colors. The spectral analyzer 32 also includes a diode array to measure the intensity of various, selected frequencies of the light from the diffraction grating. The diode array, not shown, converts the intensities of the light at various frequencies to electrical signals which are transmitted to preamplifier 34 by line 36. Electrical signals from preamplifier 34 are transmitted to electronic circuitry including a micro processor 36 to process information concerning the intensities of light at various frequencies and provide an output to a computer, not shown, via line 40.

A power supply 42 receives electrical current an outside source and provides power to the light bulbs 20 and 22 as well as to the preamplifier 34 and the micro processor 36.

The second housing 14 encloses stepper motor 44 and a backing system 50 which will be described hereinafter. The stepper motor receives instructions via electrical signals from micro processor 36 by line 52.

Figure 3:
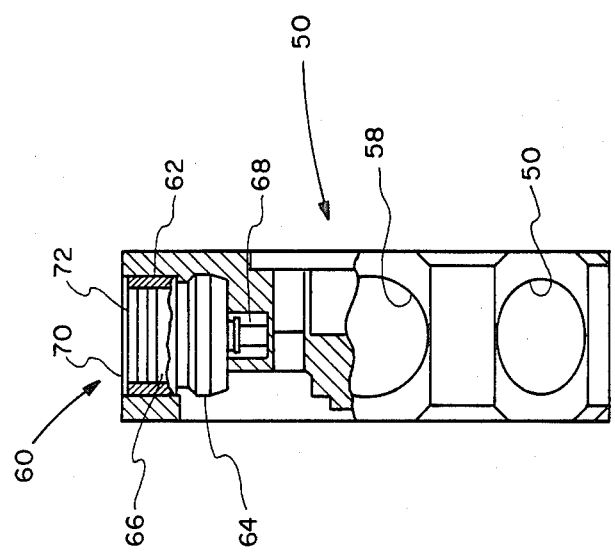
FIG. 3 is another view of the part shown in FIG. 2.
Figure 2:
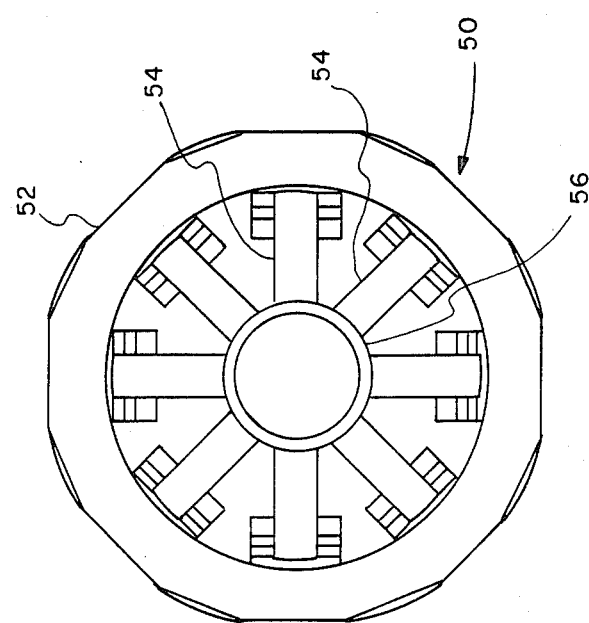
FIG. 2 is a schematic illustration of one part of the present embodiment shown in FIG. 1.

FIGS. 2 and 3 show the backing system 50 in further detail. The backing system includes a generally octagonal support member 52 which has eight spokes 54. Near the center of the support member 52 the spokes are coupled to a cylindrical member which in turn is coupled to the stepper motor 44 so that the stepper motor can operate to rotate the backing system 50 about its central axis. The support member also includes eight cylindrical ports 58 to accommodate containers 60.

With reference to FIG. 3, each of the eight containers 60 includes a hollow, generally cylindrical body 62 having a lower portion 64 shaped to fit into a port 58. The body 62 is hollow to accommodate a plunger 66 which is coupled to a rod 68 by a spring, not shown. The container 60 also includes a quartz plate 70 mounted at the upper end of the body 62. The plunger 66 fits within the upper end of the body 62 to slide therein so that a plurality of sheets of paper in the form a pad 72 can be located between the upper end of the plunger 66 and the quartz plate 70. When the pad 72 is inserted in the container 60, and the container inserted in the support member 52, the lower end of the rod 68 contacts the support member 52 so that as pressure is applied downwardly on the container 60 the spring between the rod 68 and the plunger 66 applies force upwardly on the pad 72 thereby forcing the pad against the quartz plate 70. Locking means, not shown, can be utilized in conjunction with the container 60 to hold it in place in the support member 52.

Some of the containers 60 can contain different materials in place of the pad 72. Thus the support member 52 can be rotated by the stepper motor under the control of the micro processor 36 so that when different grades of paper are being manufactured different samples are used to back the material. Also, certain standard materials can be inserted in the container 60. When standardization is required the stepper motor can rotate the support member 52 so that the appropriate standard is located beneath the housing 10.

In operation, light from the bulbs 20 and 22 impinges upon the sheet of paper 12. Some of the light is reflected directly back to the lens 30 while some of the light passes through the paper to be reflected by the material in the container 60. Light reflected from the material in the container in part returns through the paper, and some of that light is collected by the lens 30.

We have found that the use of proper materials to form the pad 72 is crucial. The pad 72 should be composed of a plurality of sheets of paper so that the pad is at least about one-sixteenth inch thick. It is important that a sufficient number of sheets be used so that the addition of sheets does not affect the optical properties of the pad.

In a paper mill which manufactures only a few different colors of paper, a plurality of pads 72 should be produced from standard sheets of paper having exactly the colors which the mill wishes to produce. These standard pads should be stored under proper conditions to insure that the color and other characteristics of the paper do not deteriorate, and when it is desired to measure the color of paper being produced, the pad having the target color, i.e. the color which the paper being produced is desired to have, is used to back the sample paper 12 when it is measured. We have found that the closer the color of the sample paper 12 to the standard sheets forming the pad 72, the more accurately our system measures the color of the sample 12.

However, if the mill manufactures many different colors of paper, it may not be practical to change the backing pad each time a different target color is desired. In this case, we have found that the use of white paper to form the pad 72 can give satisfactory results. By white paper, we mean paper which has substantially 100% reflectance of light in all parts of the visible spectrum. Thus, in measuring colored paper, i.e. paper which does not reflect all colors equally, the pad reflects substantially more light than the sample paper.

In the case of either a colored pad or a white pad, we have found that it is important that the standard sheets forming the pad 72 have substantially the same characteristics as the sample sheet 12. In particular, the scattering coefficients, $\sigma$, of the two types of sheets should be substantially the same. For example, if the sample 12 was made from groundwood pulp the standard sheets should likewise have been made from groundwood pulp, and if the sample 12 was made from chemical pulp the standard sheets should also have been. Also, it is preferable that the absorption coefficients, k, and the degrees of fluorescence of the two types of sheets should be as nearly the same as practical.

We have found that for measurement of the color of some types of paper the use of a pad of paper in the container 60 provides significantly superior results in the measurement of color as compared to using a standard white backing such as ceramic tile. We have also found that using a white pad of paper for backing the sheet often provides good results for various different colors of paper being measured. This is a significant advantage over standard backings which often show wide variability in results when the types of paper vary from one to another.

We claim:

1. A system for measuring the color of a moving sheet of material which is being produced, the system comprising:
   (a) means for causing the sheet to move;
   (b) means for illumination the sheet;
   (c) sensor means located to a first side of the sheet for receiving light from the sample material;
   (d) means for measuring the intensities of predetermined frequencies of light received by the sensor; and,
   (e) backing means for reflecting light from the sheet back toward the sheet, said backing means being constructed so that the sheet moves relative to said backing means and said backing means including backing material which is substantially the same as the sheet, said backing material being spaced apart from the sheet.

2. A system according to claim 1 wherein said sheet is paper and said backing material is a plurality of sheets of paper in the form of a pad.

3. A system according to claim 1 wherein said backing means is located to the second side of the material.

4. A system according to claim 1 wherein the backing material has substantially the same scattering coefficient as the sample material.

5. A system according to claim 1 wherein the backing material has substantially the same absorption coefficient, degree of fluorescence, and scattering coefficient as the sample material.

6. A system according to claim 1 wherein said backing means includes a quartz plate is located between the moving sheet and said backing material.

7. A process for measuring the color of a moving sheet of material which is being produced, the process comprising:
   (a) illuminating the moving sheet;
   (b) sensing light from the moving sheet;
   (c) determining the intensities of predetermined frequencies of sensed light;
   (d) locating a backing means to move relative to the sheet, the backing means including a pad formed of a plurality of sheets of standard material wherein the pad is spaced apart from the moving sheet; and
   (e) reflecting light from the moving sheet back toward the moving sheet with the backing means.

* * * * *